(12) United States Patent
Fujie et al.

(10) Patent No.: US 8,052,785 B2
(45) Date of Patent: Nov. 8, 2011

(54) INDANILINE DYE, THERMAL TRANSFER RECORDING INK SHEET, THERMAL TRANSFER RECORDING METHOD, COLOR TONER, INKJET INK, AND COLOR FILTER

(75) Inventors: Yoshihiko Fujie, Kanagawa (JP); Takashi Hoshimiya, Kanagawa (JP); Hisashi Mikoshiba, Kanagawa (JP); Naotsugu Muro, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 894 days.

(21) Appl. No.: 12/057,551

(22) Filed: Mar. 28, 2008

(65) Prior Publication Data

US 2008/0242542 A1 Oct. 2, 2008

(30) Foreign Application Priority Data

Mar. 30, 2007 (JP) .................. 2007-092235

(51) Int. Cl.
*C09D 11/00* (2006.01)
(52) U.S. Cl. ............... 106/31.43; 106/31.47; 428/195.1; 428/913; 428/914; 503/227; 8/470
(58) Field of Classification Search ............... 106/31.43, 106/31.47; 428/195.1, 913, 914; 503/227; 8/470
See application file for complete search history.

(56) References Cited

U.S. PATENT DOCUMENTS

| 5,252,530 A | * | 10/1993 | Nakamura | .................. 503/227 |
| 5,344,807 A | * | 9/1994 | Nakamura | .................. 503/227 |
| 5,346,877 A | * | 9/1994 | Nakamura | .................. 503/227 |

* cited by examiner

*Primary Examiner* — Betelhem Shewareged
(74) *Attorney, Agent, or Firm* — Sughrue Mion, PLLC (57) ABSTRACT

An indaniline dye represented by the following formula (1):

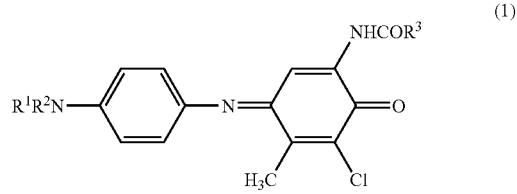

wherein $R^1$ and $R^2$ represent an unsubstituted linear or branched alkyl group having from 2 to 5 carbon atoms; $R^3$ represents an unsubstituted linear or branched alkyl group having from 1 to 3 carbon atoms; provided that the total number of the carbon atoms of $R^1$, $R^2$ and $R^3$ is 6 or 7.

6 Claims, 1 Drawing Sheet

INDANILINE DYE, THERMAL TRANSFER RECORDING INK SHEET, THERMAL TRANSFER RECORDING METHOD, COLOR TONER, INKJET INK, AND COLOR FILTER

BACKGROUND OF THE INVENTION

1. Field of the Invention

The present invention relates to a novel specific indaniline dye, and to a thermal transfer recording ink sheet, a thermal transfer recording method, a color toner, an inkjet ink and a color filter comprising or using the dye.

2. Background Art

These days, in particular, a color image-forming material is the mainstream of an image-recording material; and concretely, inkjet-type recording materials, thermal transfer-type recording materials, electrophotographic recording materials, transfer-type silver halide photosensitive materials, printing inks and recording pens are much used. In an image sensor such as CCD as photography machinery and in LCD or POP as displays, a color filter is used for recording and reproducing color images.

In a color image-recording material and a color filter, used are colorants (dyes, pigments) of three primary colors for an additive mixture process or a subtractive mixture process. At present, however, no one could find a fast colorant that has absorption characteristics capable of realizing a favorable color reproduction range and is durable to various conditions in practical use, and it is strongly desired to improve colorants.

Thermal transfer recording includes a recording system where a thermal transfer material having a thermofusible ink layer formed on a support (base film) is heated with a thermal head to thereby melt the ink for recording on an image-recording material, and a recording system where a thermal transfer material having a transferable dye-containing dye-donating layer formed on a support is heated with a thermal head to thereby thermally diffuse and transfer the dye onto an image-receiving material. In the latter thermal transfer system, the dye transfer rate may be varied by changing the energy to be applied to the thermal head, therefore facilitating gradation recording, and the system is especially advantageous for high-quality full-color recording. However, the transferable dye for use in this system has various limitations, and only an extremely few dyes are known capable of satisfying all the necessary performance requirements.

The performance requirements include, for example, spectral characteristics favorable for color reproduction, easy transferability, fastness to light and heat, fastness to various chemicals, easy producibility, and easy workability to construct thermal transfer recording materials. However, conventional specific dyes that have been proposed as those having spectral characteristics favorable for color reproduction and having fastness to light and heat (for example see Patent JP-A 1-225592 and JP-A 63-189289) could not be on a satisfactory level, and further improvements are strongly desired.

In color copiers and color laser printers to be driven by eleotrophotography, in general, a toner is widely used that comprises a colorant dispersed in resin particles. The performance requirements for the co or toner include absorption characteristics capable of realizing a preferred color reproduction range, especially high transmittance (transparency) required in use in overheat projectors (hereinafter referred to as OHP), and various fastness requirements under environmental conditions in practical use. A toner comprising a pigment colorant dispersed in particles has been proposed (for example, see JP-A 62-157051, JP-A 62-255956 and JP-A 6-118715). The toner of the type may have excellent light fastness, but may readily aggregate as being insoluble and is problematic in point of the transparency reduction and the transmitted color shift. On the other hand, a toner comprising a specific dye as a colorant has also been proposed (for example, see JP-A 3-276161, JP-A2-207274 and, JP-A 2-207273), and the toner of the type has high transparency and is free from the problem of color shift contrary to the above, but is problematic in point of the light fastness.

An inkjet recording method has been rapidly popularized and is being developed further more, since its material cost is low, it enables high-speed recording, it is noiseless in recording operation, and it facilitates color recording.

The inkjet recording method includes a continuous system of continuously jetting out ink droplets and an on-demand system of jetting out ink droplets in accordance with image information signals; and the jetting system includes a system of jetting out ink droplets under pressure given thereto by a piezo device, a system of jetting out ink droplets by generating bubbles in ink by heat, a system of using ultrasonic waves, and a system of electrostatically sucking and jetting out ink droplets. As the inkjet recording ink, usable is water-base ink, oily ink, or solid (fusible) ink.

The requirements for the colorant to be used in the inkjet recording ink are that it well dissolves or disperses in solvent, it enables high-density recording, its color is good, it is fast to light, heat, active gases in the environment (e.g., oxidizing gas such as NOx, SOx, ozone), it is fast to water and chemicals, it may well fix in image-receiving material and hardly blurs it, it is well storable as ink, it is nontoxic, its purity is high, and it is inexpensive and easily available. However, it is extremely difficult to obtain a colorant that satisfies all these requirements at a high level. In particular, it is strongly desired to obtain a colorant that has a good cyan color tone, has high solubility, and is fast to light, humidity and heat, especially highly fast to light.

A color filter is required to have high transparency, for which, therefore, employed is a dyeing method of coloration with a dye. For example, a method that comprises patterning exposure and development of a dyeable photoresist to form a pattern, and then dyeing it with a filter color dye is successively repeated for all filter colors to produce a color filter. Apart form the dyeing method, a method of using a positive resist may also be employed for producing a color filter. The color filters produced according to these methods may have high transparency and excellent optical properties as using dyes, but their light fastness and heat resistance are limited. Accordingly, a colorant having excellent fastness and having high transparency is desired. On the other hand, a method of using an organic pigment having excellent light fastness and heat resistance in place of dye is widely known, but pigment-containing color filters could hardly have good optical properties like those of dye-containing color filters.

Common to those for use in the above-mentioned applications, the dyes are desired to have the following properties. Specifically, they have a color favorable for color reproduction, they have an optimum spectral absorption, their fastness such as light fastness, moisture fastness, chemical fastness is good, their solubility is high.

For use in thermal transfer recording, dyes having a specific indaniline skeleton have been proposed (for example, see Japanese Patent 2,572,025 and European Patent 147,747). However, the dyes could not always satisfy the above-mentioned requirements for their properties on a satisfactory level, and further investigations are desired.

SUMMARY OF THE INVENTION

An object of the invention is to provide a thermal transfer recording ink sheet and a thermal transfer recording method, in which an indaniline dye having excellent spectral characteristics with sharp absorption and having high fastness is used to satisfy all the requirements of excellent color reproducibility, image storability and transfer sensitivity in print samples. Another object of the invention is to provide the indaniline dye having excellent solubility. Still another object of the invention is to provide a color toner, an inkjet ink and a color filter comprising the indaniline dye. Still another object of the invention is to provide a novel indaniline dye having a specific substituent, which has especially excellent spectral characteristics with sharp absorption and has high fastness.

The present inventors have assiduously studied and, as a result, have found that the above-mentioned objects can be attained by the following constitution:

[1] An indaniline dye represented by the following formula (1):

wherein $R^1$ and $R^2$ each independently represent an unsubstituted linear or branched alkyl group having from 2 to 5 carbon atoms; $R^3$ represents an unsubstituted linear or branched alkyl group having from 1 to 3 carbon atoms; provided that the total number of the carbon atoms of $R^1$, $R^2$ and $R^3$ is 6 or 7.

[2] A thermal transfer recording ink sheet containing the indaniline dye of the above [1].

[3] A thermal transfer recording method comprising forming an image by use of the thermal transfer recording ink sheet of the above [2] on an image-receiving material comprising a polymer-containing ink-receiving layer on a support.

[4] A color toner containing the indaniline dye of the above [1].

[5] An inkjet ink containing the indaniline dye of the above [1].

[6] A color filter containing the indaniline dye of the above [1].

According to the invention, there are provided a novel indaniline dye satisfying all the requirements of excellent spectral characteristics with sharp absorption, high fastness and excellent transfer sensitivity; a thermal transfer recording ink sheet containing the indaniline dye; and a thermal transfer recording method using it. Accordingly, the invention provides a thermal transfer recording ink sheet and a thermal transfer recording method capable of satisfying all the requirements of excellent color reproducibility, image storability and transfer sensitivity in print samples. Further, the invention provides a color toner, an inkjet ink and a color filter comprising the indaniline dye.

BEST MODE FOR CARRING OUT THE INVENTION

DESCRIPTION OF THE PREFERRED EMBODIMENTS

The thermal transfer recording ink sheet, the color toner, the inkjet ink and the color filter and also the indaniline dye for use in these of the invention are described in detail hereinunder.

The description of the constitutive elements of the invention given hereinunder is for some typical embodiments of the invention, to which, however, the invention should not be limited. In this description, the numerical range expressed by the wording "a number to another number" means the range that falls between the former number indicating the lowermost limit of the range and the latter number indicating the uppermost limit thereof.

[Indaniline Dye of formula (1)]

The indaniline dye of formula (1) of the invention is described in detail.

The indaniline dye of the invention is a novel dye. Concretely, the dye is characterized in that it does not have a substituent in the aromatic ring in the aniline moiety and that the total number of the carbon atoms constituting $R^1$, $R^2$ and $R^3$ is 6 or 7 (that is, the molecular weight of the dye is from 374to388). The indaniline dye having the characteristics exhibits a good cyan color of high visibility, and satisfies all the requirements of good solubility in water and good transfer sensitivity in thermal transfer recording. The indaniline dye of formula (1) has excellent color expressibility, solubility and transfer sensitivity and is therefore favorable for use in thermal transfer recording ink sheets, and in addition, it is favorable for use in other applications (e.g., color toner, inkjet ink, color filter).

In formula (1) $R^1$ and $R^2$ each independently represent an unsubstituted linear or branched alkyl group having from 2 to 5 carbon atoms. Concretely, the group includes an ethyl group, an n-propyl group, an isopropyl group, an n-butyl group, an isobutyl group, an s-butyl group.

In formula (1), $R^3$ represents an unsubstituted linear or branched alkyl group having from 1 to 3 Carbon atoms. Concretely, it includes a methyl group, an ethyl group, an n-propyl group, an isopropyl group.

$R^1$ and $R^2$ each independently represent an unsubstituted linear or branched alkyl group having from 2 to 3 carbon atoms, more preferably an unsubstituted linear alkyl group having from 2 or 3 carbon atoms.

$R^3$ is preferably an unsubstituted linear alkyl group having from 1 to 3 carbon atoms, more preferably an unsubstituted alkyl group having 1 or 2 carbon atoms.

Regarding the preferred combination of the substituents (combination of $R^1$, $R^2$ and $R^3$) in the indaniline dye of formula (1) of the invention, it is desirable that at least one of these substituents in the indaniline dye is the above-mentioned preferable group, more preferably more various substituents are the above-mentioned preferred groups, most preferably all the substituents are the above-mentioned preferred groups.

One preferred combination is that $R^1$ is an unsubstituted linear alkyl group having from 2 to 4 carbon atoms, $R^2$ is an unsubstituted linear alkyl group having from 2 to 4 carbon atoms, $R^3$ is an unsubstituted alkyl group having from 1 to 3 carbon atoms.

A more preferred combination is that $R^1$ is an unsubstituted linear alkyl group having 2 or 3 carbon atoms, $R^2$ is an unsubstituted linear alkyl group having 2 or 3 carbon atoms, $R^3$ is an unsubstituted alkyl group having 1 or 2 carbon atoms.

A most preferred combination is that all of $R^1$, $R^2$ and $R^3$ are ethyl groups, or $R^1$ and $R^2$ are both n-propyl groups and $R^3$ is a methyl group.

The molecular weight of the indaniline dye of formula (1) is preferably from 370 to 390 from the viewpoint of the solubility and the thermal diffusibility thereof.

Specific examples of the indaniline dye of formula (1) of the invention are shown below, by which, however, the invention should not be limitatively interpreted.

(1)

(2)

(3)

(4)

(5)

(6)

(7)

These indaniline dyes may be produced in a per-se well-known production method. For example, they may be readily produced by oxidatively coupling a phenol of the following formula (B) and a phenylenediamine of the following formula (C) in the presence of an oxidizing agent such as silver chloride, persulfate, red prussiate under a basic condition. Concretely, it is demonstrated in Examples given hereunder.

(B)

(C)

(In formulae (B) and (C), $R^1$, $R^2$ and $R^3$ have the same meanings as those in formula (1).)

The indaniline dye of the invention is preferably used as a cyan color of three primary colors.

The maximum absorption wavelength of the indaniline dye of the invention preferably falls within a range of from 580 to 660 nm, more preferably from 600 to 640 nm.

[Thermal Transfer Recording Ink Sheet]

The thermal transfer recording ink sheet of the invention is characterized by containing the dye of formula (1). The thermal transfer recording ink sheet generally has a structure with a dye-donating layer formed on a support, in which the dye-donating layer contains a dye of formula (1). The thermal transfer recording ink sheet of the invention may be produced as follows: A dye of formula (1) is dissolved in a solvent along with a binder therein or dispersed as particles in a solvent, thereby preparing an ink liquid, then the ink liquid is applied onto a support and suitably dried to form a dye-donating layer thereon.

As the support of the thermal transfer recording ink sheet of the invention, any ordinary one heretofore used as a support for ink sheets may be suitably selected and used. For example, the material described in JP-A 7-137466, paragraph [0050] may be favorably used. The thickness of the support is preferably from 2 to 30 μm.

Not specifically defined, the binder resin usable in the dye-donating layer of the thermal transfer recording ink sheet of the invention may be any one having high heat resistance and not interfering with the transference of the dye into an image-receiving material when heated. For example, its preferred examples are described in JP-A 7-137466, paragraph [0049]. The solvent for dye-donating layer formation may also be any conventional known one; and those described in JP-A 7-137466, Examples are favorably used also herein.

The content of the dye of formula (1) in the dye-donating layer is preferably from 0.03 to 1.0 g/m$^2$, more preferably from 0.1 to 0.6 g/m$^2$. The thickness of the dye-donating layer is preferably from 0.2 to 5 μm, more preferably from 0.4 to 2 μm.

The thermal transfer recording ink sheet of the invention may have any other layer than the dye-donating layer within a range not too much detracting from the effect of the invention. For example, an interlayer may be provided between the support and the dye-donating layer; or a back layer may be provided on the surface of the support opposite to the side of the dye-donating layer (this is hereinafter referred to as "back surface"). The interlayer includes, for example, an undercoating layer, and a diffusion-preventing layer for preventing the dye from diffusing toward the support (hydrophilic barrier layer). The back layer is, for example, a heat-resistant slip layer, which is for preventing a thermal head from sticking to the ink sheet.

In case where the invention is applied to thermal transfer recording material that enables full-color image recording, it is desirable that a cyan ink sheet containing a thermal diffusible cyan dye capable of forming cyan images, a magenta ink sheet containing a thermal diffusible magenta dye capable of forming magenta images, and a yellow ink sheet containing a thermal diffusible yellow dye capable of forming yellow images are formed successively on a support. If desired, an ink sheet containing a black image-forming substance may be further formed.

As the thermal diffusible magenta dye-containing magenta ink sheet for forming magenta images, for example, preferably used are those described in U.S. Pat. No. 5,789,560. As the thermal diffusible yellow dye-containing yellow ink sheet for forming yellow images, for example, preferably used are those described in JP-A 1-225592.

[Thermal Transfer Recording]

In thermal transfer recording by the use of the thermal transfer recording ink sheet of the invention, a heating unit such as a thermal head and an image-receiving material are used as combined. Specifically, heat energy is applied to the ink sheet from a thermal head according to an image recording signal, and the dye in the part having received the heat energy is transferred to and fixed in an image-receiving material to attain image recording. The image-receiving material generally has a constitution with a polymer-containing ink-receiving layer formed on a support. As the constitution and the constitutive components of the image-receiving material, for example, preferably used are those described in JP-A 7-137466, paragraphs [0056] to [0074].

[Color Toner]

The color toner of the invention is characterized by containing the dye of formula (1). As the binder resin for color toner into which the dye (preferably indaniline dye) of formula (1) of the invention is introduced, usable is any and every binder for general use in toner. For example, it includes styrene resin, acrylic resin, styrene/acrylic resin, polyester resin. For the purpose of improving the flowability of the toner and for static control thereof, an inorganic fine powder or organic fine particles may be added to the toner as external additives. Preferably used are silica particles and titania particles of which the surfaces are processed with an alkyl group-containing coupling agent or the like. Preferably, the particles have a number-average primary particle size of from 10 to 500 nm; and also preferably, the particles are added to the toner in an amount of from 0.1 to 20% by mass.

As the lubricant, any and every lubricant heretofore used in toner may be used herein. Concretely, it includes olefins such as low-molecular-weight polypropylene, low-molecular-weight polyethylene, ethylene-propylene copolymer; and microcrystalline wax, carnauba wax, Sasol wax, paraffin wax. Preferably, the lubricant is added to the toner in an amount of from 1 to 5% by mass.

If desired, a charge-controlling agent may be added to the toner, and it is preferably colorless from the viewpoint of the colorability of the toner. For example, herein usable are those having a quaternary ammonium salt structure or a calixarene structure.

The carrier may be any of a non-coated carrier formed of magnetic material particles alone of iron, ferrite or the like; or a resin-coated carrier prepared by coating the surfaces of magnetic material particles with resin or the like. Regarding the mean particle size thereof, the carrier preferably has a volume-average particle size of from 30 to 150 μm.

The image-forming method to which the toner of the invention is applicable is not specifically defined. For example, the toner is applicable to an image-forming method that comprises repeatedly forming a color image on a photoreceptor followed by transferring it; and a color image-forming method that comprises transferring an image formed on a photoreceptor successively onto an intermediate transfer medium thereby forming a color image on the intermediate transfer medium, followed by transferring the image onto an image-forming member such as paper.

[Inkjet Ink]

The inkjet ink of the invention is characterized by containing the dye of formula (1). The ink of the invention may be produced by dissolving and/or dispersing the dye of formula (1) in an oleophilic medium or an aqueous medium, and preferably an aqueous medium is used. The ink of the invention contains the dye having excellent spectral characteristics and fastness as so mentioned in the above, and is therefore favorably used as an inkjet recording ink. If desired, other additives may be added to the ink within a range not detracting from the effect of the invention. The additives may be known additives, including, for example, a drying inhibitor (wetting agent), an antifading agent, a emulsion stabilizer, a penetration promoter, a UV absorbent, a preservative, an antifungal agent, a pH controlling agent, a surface tension controlling agent, a defoaming agent, a viscosity controlling agents a dispersant, a dispersion stabilizer, a rust inhibitor, a chelating agent. In general, these various additives are added to the dye dispersion after its preparation, but as the case may be, they may be added to an oily phase or an aqueous phase in preparing the dye dispersion.

The drying inhibitor is favorably used for the purpose of preventing the inkjet ink from drying at the ink-jetting orifice of the nozzle used in an inkjet recording system.

The drying inhibitor is preferably a water-soluble organic solvent having a vapor pressure lower than water. Its concrete examples include polyalcohols such as typically ethylene glycol, propylene glycol, diethylene glycol, polyethylene glycol, thiodiglycol, dithiodiglycol, 2-methyl-1,3-propanediol, 1,2,6-hexanetriol, acetylene glycol derivative, glycerin, trimethylolpropane; polyalcohol lower alkyl ethers such as ethylene glycol monomethyl (or ethyl) ether, diethylene glycol monomethyl (or ethyl) ether, triethylene glycol monoethyl (or butyl) ether; heterocyclic compounds such as 2-pyrrolidone, N-methyl-2-pyrrolidone, 1,3-dimethyl-2-imidazolidinone, N-ethylmorpholine; sulfur-containing compounds such as sulfolane, dimethyl sulfoxide, 3-sulfolene; polyfunctional compounds such as diacetone alcohol, diethanolamine; and urea derivatives. Of those, more preferred are polyalcohols such as glycerin, diethylene glycol. One or more of the above drying inhibitors may be used either singly or as combined. The drying inhibitor may be in the ink preferably in an amount of from 10 to 50% by mass.

The penetration promoter is favorably used for the purpose of more rapidly penetrating the inkjet ink into paper. As the penetration promoter, usable are alcohols such as ethanol, isopropanol, butanol, di (tri) ethylene glycol monobutyl ether, 1,2-hexanediol; sodium laurylsulfate, sodium oleate, non-ionic surfactant. When the agent is in the ink in an amount of from 5 to 30% by mass, then it is generally sufficiently effective. Preferably, the agent is used in an amount not causing print blur and print through.

The UV absorbent is used for the purpose of improving the image storability. The UV absorbent includes benzotriazole compounds as in JP-A 58-185677, 61-190537, 2-782, 5-197075, 9-34057; benzophenone compounds as in JP-A 46-2784, 5-194483, U.S. Pat. No. 3,214,463; cinnamic acid compounds as in JP-B 48-30492, 56-21141, JP-A 10-88106; triazine compounds as in JP-A 4-298503, 8-53427, 8-239368, 10-182621, JP-T 8-501291; and also the compounds described in Research Disclosure No. 24239, and compounds capable of absorbing UV rays to emit fluorescent light, or that is, fluorescent brighteners such as typically stilbene compounds and benzoxazole compounds.

The antifading agent is used for the purpose of improving the image storability. As the antifading agent, usable are various organic or metal complex-type antifading agents. The organic antifading agent includes hydroquinones, alkoxyphenols, dialkoxyphenols, phenols, anilines, amines, indanes, chromans, alkoxyanilines, and heterocyclic compounds; and the metal complex includes nickel complexes and zinc complexes. More concretely, herein usable are the compounds described in the patent references cited in Research Disclosure No. 17643, Items VII-Ito J, ibid., No.15162, ibid., No. 18716, page 650, left column, ibid., No. 36544, page 527, ibid., No. 307105, page 872, ibid., No. 15162; and the compounds falling within the scope of the typical compounds of the formula and the examples of the compounds described in JP-A 62-215272, pp. 127 to 137.

The rust inhibitor includes sodium dehydroacetate, sodium benzoate, sodium pyridinethione-1-oxide, ethyl p-hydroxybenzoate, 1,2-benzisothiazolin-3-one and its salts. Preferably, this is in the ink in an amount of from 0.02 to 1.00% by mass.

As the pH controlling agent, usable are neutralizing agents (organic base, inorganic alkali). For the purpose of improving the storage stability of the inkjet ink, the pH controlling agent is preferably added to the inkjet ink so that the ink could have a pH of from 6 to 10, more preferably from 7 to 10.

The surface tension controlling agent may be a nonionic, cationic or anionic surfactant. Preferably, the surface tension of the inkjet ink containing the coloring composition of the invention is from 20 to 60 mN/mr, more preferably from 25 to 45 mN/m. The viscosity of the inkjet ink of the invention is preferably at most 30 mPa·s r more preferably so controlled as to be at most 20 mPa·s.

Preferred examples of the surfactant include anionic surfactants such as fatty acid salts, alkylsulfate ester salts, alkylbenzenesulfonic acid salts, alkylnaphthalenesulfonic salts, dialkylsulfosuccinic acid salts, alkylphosphate ester salts, naphthalenesulfonic acid/formalin condensates, polyoxyethylene alkylsulfate ester salts; and nonionic surfactants such as polyoxyethylene alkyl ethers, polyoxyethylene alkylaryl ethers, polyoxyethylene fatty acid esters, sorbitan fatty acid esters, polyoxyethylene sorbitan fatty acid esters, polyoxyethylene alkylamines, glycerin fatty acid esters, oxyethyleneoxypropylene block copolymers. Also preferred are SURFYNOLS (trade name by Air Products & Chemicals) that are acetylene-type polyoxyethylene oxide surfactants. Also preferred are amine oxide-type ampholytic surfactants such as N,N-dimethyl-N-alkylamine oxide. Further usable herein are the surfactants described in JP-A 59-157636, pp. 37-38, and Research Disclosure No. 308119 (1989).

As the defoaming agent, optionally used herein are fluorine compounds, silicone compounds, and chelating agents such as EDTA.

In case where the dye of formula (1) is dispersed in an aqueous medium, it is desirable that coloring particles containing the compound and an oil-soluble polymer are dispersed in an aqueous medium as in JP-A 11-286637, 2001-240763, 2001-262039, 2001-247788, or the dye of formula (1) dissolved in a high-boiling-point organic solvent is dispersed in an aqueous medium as in JP-A 2001-262018, 2001-240763, 2001-335734, 2002-80772. Regarding the concrete method of dispersing the dye of formula (1) in an aqueous medium, as well as the oil-soluble polymer, the high-boiling-point organic solvent and the additives to be used, and their amount, those described in the above-mentioned patent references are employable herein. As the case may be, the bisazo compound may be dispersed as fine particles directly as it is solid. In dispersing then, a dispersant and a surfactant may be used.

As the dispersing device, usable are simple stirrers, and also impellers, in-line stirrer mills (e.g., colloid mill, ball mill, sand mill, attritor, roll mill, agitator mill), ultrasonic stirrers, high-pressure emulsification dispersers (high-pressure homogenizers; as commercial devices, available are Gaulin homogenizer, Microfluidizer, DeBEE 2000 (by BEE International)). Regarding the method of preparing the above-mentioned inkjet recording ink, its details are described also in JP-A 5-148436, 5-295312r 7-97541, 7-82515, 7-118584, 11-286637, 2001-271003, in addition to the above-mentioned patent references; and these descriptions are applicable to the preparation of the inkjet recording ink of the invention.

As the aqueous medium, usable is a mixture comprising water as the main ingredient and optionally containing a water-miscible organic solvent added thereto. Examples of the water-miscible organic solvent include alcohols (e.g., methanol, ethanol, n-propanol, isopropanol, butanol, isobutanol, sec-butanol, t-butanol, pentanol, hexanol, cyclohexanol, benzyl alcohol), polyalcohols (e.g., ethylene glycol, diethylene glycol, triethylene glycol, polyethylene glycol, propylene glycol, dipropylene glycol, polypropylene glycol, butylene glycol, hexanediol, pentanediol, glycerin, hexanetriol, thiodiglycol), glycol derivatives (e.g., ethylene glycol monomethyl ether, ethylene glycol monoethyl ether, ethylene glycol monobutyl ether, diethylene glycol monomethyl ether, diethylene glycol monobutyl ether, propylene glycol monomethyl ether, propylene glycol monobutyl ether, dipropylene glycol monomethyl ether, triethylene glycol monomethyl ether, ethylene glycol diacetate, ethylene glycol monomethyl ether acetate, triethylene glycol monomethyl ether, triethylene glycol monoethyl ether, ethylene glycol monophenyl ether), amines (e.g., ethanolamine, diethanolamine, triethanolamine, N-methyldiethanolamine, N-ethyldiethanolamine, morpholine, N-ethylmorpholine, ethylenediamine, diethylenetriamine, triethylenetetramine, polyethyleneimine, tetramethylpropylenediamine), and other polar solvents (e.g., formamide, N,N-dimethylformamide, N,N-dimethylacetamide, dimethyl sulfoxide, sulfolane, 2-pyrrolidone, N-methyl-2-pyrrolidone, N-vinyl-2-pyrrolidone, 2-oxazolidone, 1,3-dimethyl-2-imidazolidinone, acetonitrile, acetone). Two or more of the above-mentioned water-miscible organic solvents may be combined for use herein.

[Color Filter]

The color filter of the invention is characterized by containing the dye of formula (1). For producing the color filter, employable is a method of first forming a pattern with a photoresist and then dying it; or a method of forming a pattern with a photoresist to which a colorant is added, as in JP-A 4-163552, 4-128703, 4-175753. As the method of introducing the dye of formula (1) into the color filter of the invention, any of the above methods is employable, but preferred is the method described in JP-A 4-175753, 6-35182. The method comprises applying a positive photoresist composition containing a thermosetting resin, a quinonediazide compound, a crosslinking agent, a colorant and a solvent, onto a support, then exposing it through a mask, developing the exposed area to form a positive resist pattern, then exposing the entire surface of the positive resist pattern to light, and thereafter curing the thus-exposed positive resist pattern to produce a color filter. Also employable is a method of forming a black matrix in an ordinary manner thereby obtaining an RGB primary color filter or an Y.M.C complementary color filter.

For the thermosetting resin, the quinonediazide compound, the crosslinking agent and the solvent to be used in the above and their amount, preferred are those described in the above-mentioned patent references.

EXAMPLES

The characteristics of the invention are described more concretely with reference to Production Examples and Examples given below.

In the following Examples, the material used, its amount and the ratio, the details of the treatment and the treatment process may be suitably modified or changed not overstepping the scope of the invention. Accordingly, the invention should not be limitatively interpreted by the Examples mentioned below.

Example 1

Production and Evaluation of Dye

<Production of Compound (1)>

Compound (1)

(Production of Compound (1))

3,5-Dichloro-2-hydroxy-4-methylphenylpropionamide (4.96 g, 0.02 mol), N,N-diethylphenylenediamine sulfate (6.28 g, 0.024 mol) and sodium carbonate (30 g) were dissolved in ethyl acetate (320 mL), ethanol (160 mL) and water (240 mL), and a solution prepared by dissolving ammonium persulfate (5.58 g) in water (40 mL) was gradually dropwise added thereto. Next, this was stirred at room temperature for 1 hours and the precipitated crystal was taken out by filtration, washed with water, and recrystallized with ethanol to obtain a crystal of the compound (1) (yield: 4.18 g, 56%; melting point: 162° C.). λmax of the compound (1) (in ethyl acetate solution) was 626 nm.

<Production of Compounds (2), (3) and (4)>

Compounds (2), (3) and (4) were produced according to the method of the above Production Example. Their structures were identified through $^1$H NMR spectrometry and MS spectrometry. Others than these compounds could also be produced according to the method of the above-mentioned Production Example from the chemical viewpoint.

<Evaluation>

The thus-obtained compounds (1) to (4) were analyzed for absorption spectrometry in an ethyl acetate solution (concentration: $1 \times 10^{-6}$ mol/L, optical path length; 10 mm). The data of the maximum absorption wavelength of the compounds are shown in the following Table 1. The data of $^1$H NMR spectrometry (in heavy chloroform) and MS spectrometry of the obtained compounds (1) to (4) are shown in Table 1 below.

TABLE 1

| Dye | Maximum Absorption Wavelength (nm) | $^1$H NMR δ(ppm) | MS M+ |
|---|---|---|---|
| (1) | 626 | 1.2(3 + 6H), 2.4(2H), 2.5(3H), 3.4(4H), 6.7(2H), 7.2(2H), 8.2(1H), 8.4(1H) | 374 |
| (2) | 627 | 1.2(3 + 6H), 1.4(2H), 2.4(2H), 2.5(3H), 3.4(4H), 6.7(2H), 7.2(2H), 8.2(1H), 8.4(1H) | 388 |
| (3) | 627 | 1.2(6 + 6H), 2.4(1H), 2.5(3H), 3.4(4H), 6.7(2H), 7.2(2H), 8.2(1H), 8.4(1H), | 388 |
| (4) | 626 | 1.2(6H), 1.4(4H), 2.4(3H), 2.5(3H), 3.4(4H), 6.7(2H), 7.2(2H), 8.2(1H), 8.4(1H) | 388 |

Example 2

Construction and Evaluation of Thermal Transfer Recording Ink Sheet

<Construction of Thermal Transfer Recording Ink Sheet>

A polyester film (Lumirror, trade name by Toray) having a thickness of 6.0 μm and processed for heat-resistant lubrication with a thermosetting acrylic resin (thickness 1 μm) on its back was used as a support. Using a wire bar coater, a dye-donating layer-forming coating composition mentioned below was applied onto the surface of the film to form thereon a layer having a dry thickness of 1 μm, thereby constructing an ink sheet 1.

| (Dye-Donating Layer-Forming Coating Composition) | |
|---|---|
| Compound (1) | 5.5 mas. pts. |
| Polyvinylbutyral Resin (Eslec BX-1, trade name by Sekisui Chemical Industry) | 4.5 mas. pts. |
| Methyl ethyl ketone/toluene (1/1) | 90 mas. pts. |

Next, ink sheets 2 to 4 of the invention and comparative ink sheets 5 to 10 were constructed in the same manner as that for the ink sheet 1, for which, however, the compound (1) was changed to the dye shown in Table 2 below. The dye solubility was ranked in three, A (easily soluble), B (soluble), C (difficult to dissolve, but soluble). The results are shown in Table 2.

<Construction of Image-Receiving Material>

Synthetic paper (Yupo FPG200, trade name by Yupo Corporation, thickness: 200 μm) was used as a support. A white interlayer-forming coating composition and a receiving layer-forming coating composition mentioned below were applied in that order onto one surface of the support, using a bar coater. Their amount was so controlled that the white interlayer could have a dry thickness of 1.0 g/m² and the receiving layer could have a dry thickness of 4.0 g/m². The layers were dried at 110° for 30 seconds each.

| (White Interlayer-Forming Coating Composition) | |
| --- | --- |
| Polyester resin (Vylon 200, trade name by TOYOBO) | 10 mas. pts. |
| Fluorescent brightener (Uvitex OB, trade name by Ciba-Geigy) | 1 mas. pt. |
| Titanium oxide | 30 mas. pts. |
| Methyl ethyl ketone/toluene (1/1) | 90 mas. pts. |
| (Receiving Layer-Forming Coating Composition) | |
| Vinyl chloride-vinyl acetate resin (Solbine A, trade name by Nisshin Chemical Industry) | 100 mas. pts. |
| Amino-modified silicone (X22-3050E, trade name by Shin-etsu Chemical Industry) | 5 mas. pts. |
| Epoxy-modified silicone (X22-300E, trade name by Shin-etsu Chemical Industry) | 5 mas. pts. |
| Methyl ethyl ketone/toluene (= 1/1) | 400 mas. pts. |
| Benzotriazole-type UV absorbent (Tinuvin 900, trade name by Ciba Speciality Chemicals) | 5 mas. pts. |

<Image Recording and Evaluation>

The ink sheet 1 and the image-receiving material constructed as above were combined in such a manner that the dye-donating layer could face the image-receiving layer, and this was printed using a thermal head applied to the back of the dye-donating material. The output power of the thermal head was 0.25 W/dot, pulse width was from 0.15 to 15 msec, the dot density was 6 dots/mm. In that manner, the cyan dye was imagewise fixed on the image-receiving layer of the image-receiving material, and as a result, a sharp image print with no transfer unevenness was obtained. The ink sheets 2 to 8 were used in place of the ink sheet 1, tested for image recording.

The color of the obtained image was observed by eyes to evaluate in 2 ranks as follows: Excellent cyan color that is easily detected A; cyan color having a slight blue color B. The solid density (100% dot density) of each image was measured as the status A reflection density thereof, and the samples were evaluated for their transferability in 3 ranks, as follows: Those having a reflection density of at least 1.8 are excellent, A; those having from 1.6 to less than 1.8 are good, B; those having from 1.0 to less than 1.6 are average, C. The results are shown in Table 2 below.

Next, the recorded samples were exposed to an Xe light (17000 lux) for 7 days, and rested for the light stability (light fastness) of the recorded images. After the exposure, the status A reflection density of the part of each sample having an original status A reflection density of 1.0 before the exposure was measured, and the retention (by percentage) to the reflection density of 1.0 after exposure to that before exposure indicates the image stability. With the retention percentage, the samples were ranked in three, A (from 80% to less than 100%), B (from 60% to less than 80%), C (less than 60%). The results are shown in Table 2 below.

Comparative Dye 1 (in formula (1), the total number of the carbon atoms of $R^1$, $R^2$ and $R^3$<6):

Comparative Dye 2 (in formula (1), the total number of the carbon atoms of $R^1$, $R^2$ and $R^3$>7):

Comparative Dye 3 (dye described in German Patent 3524519):

Comparative Dye 4 (dye described in EP 147747):

TABLE 2

| Ink Sheet | Dye | Solubility | Color | Transferability | Light Fastness | Remarks |
| --- | --- | --- | --- | --- | --- | --- |
| 1 | (1) | A | A | A | A | the Invention |
| 2 | (2) | A | A | A | A | the Invention |
| 3 | (3) | A | A | A | A | the Invention |
| 4 | (4) | A | A | A | A | the Invention |
| 5 | Comparative Dye 1 | C | A | B | A | Comparative Example |
| 6 | Comparative Dye 2 | A | A | B | A | Comparative Example |
| 7 | Comparative Dye 3 | A | A | A | B | Comparative Example |
| 8 | Comparative Dye 4 | A | B | A | A | Comparative Example |
| 9 | Comparative Dye 5 | A | B | A | A | Comparative Example |
| 10 | Comparative Dye 6 | B | A | B | B | Comparative Example |

Comparative Dye 5 (dye described in Japanese Patent 2572025):

Comparative Dye 6 (dye described in JP-A 60-151097):

As a result of the above image recording test, it is known that the images transferred onto the image-receiving layer from the ink sheets having the indaniline dye of formula (1) of the invention has a sharp color, and as compared with those from the comparative dyes, the images have more improved stability to light and have excellent image storability.

Unexpectedly, in addition, it is known that, as compared with the comparative dyes, the indaniline dyes of formula (1) of the invention have more excellent solubility, and therefore can greatly reduce the load in dissolution in ink sheet construction, and that the transfer sensitivity of the dyes is excellent and therefore the dyes can solve both the problems of the solubility and the transferability that have heretofore been said difficult to solve.

Example 3

Formation and Evaluation of Color Toner

<Formation of Color Toner>

3 parts by mass of an indaniline dye of the invention (compound (1)) and 100 parts by mass of a toner resin [styrene-acrylate copolymer, Himer TB-1000F (trade name by Sanyo Chemical)] were mixed and ground in a ball mill, then melted and kneaded under heat at 150° C., and after cooled, this was roughly ground with a hammer mill, and then finely ground with an air jet-type grinder. Further classified, particles of from 1 to 20 μm in size were selected to be a toner.

<Evaluation>

10 parts by mass of the toner was uniformly mixed with 900 parts by mass of a carrier iron powder (EFV250/400, trade name by Nippon Iron Powder) to prepare a developer. The developer was tested for copying with a dry-type plain paper electrophotographic copier (NP-5000, trade name by Canon). As a result, the developer had excellent spectral characteristics and had excellent properties as toner.

Example 4

Formation and Evaluation of Inkjet Ink

<Formation of Inkjet ink>

An indaniline dye of the invention (compound (1)) (5.63 g) and sodium dioctylsulfosuccinate (7.04 g) were dissolved in a high-boiling-point organic solvent mentioned below (S-2) (4.22 g), a high-boiling-point organic solvent mentioned below (S-11) (5.63 g) and ethyl acetate (50 ml) at 70° C. With stirring with a magnetic stirrer, deionized water (500 ml) was added to the solution to produce an oil-in-water crude particle dispersion.

Next, the crude particle dispersion was led to pass through a microfluidizer (by MICROFLUIDEX INC) five times under a pressure of 60 MPa to be fine particles, and the thus-prepared emulsion was evaporated for solvent removal with a rotary evaporator until it gave no ethyl acetate odor.

Diethylene glycol (140 g), glycerin (50 g), SURFYNOL 465 (trade name by Air Products & Chemicals) (7 g) and deionized water (900 ml) were added to the fine emulsion of the hydrophobic dye thus obtained as above, thereby producing an inkjet ink.

<Evaluation>

Figure 1:
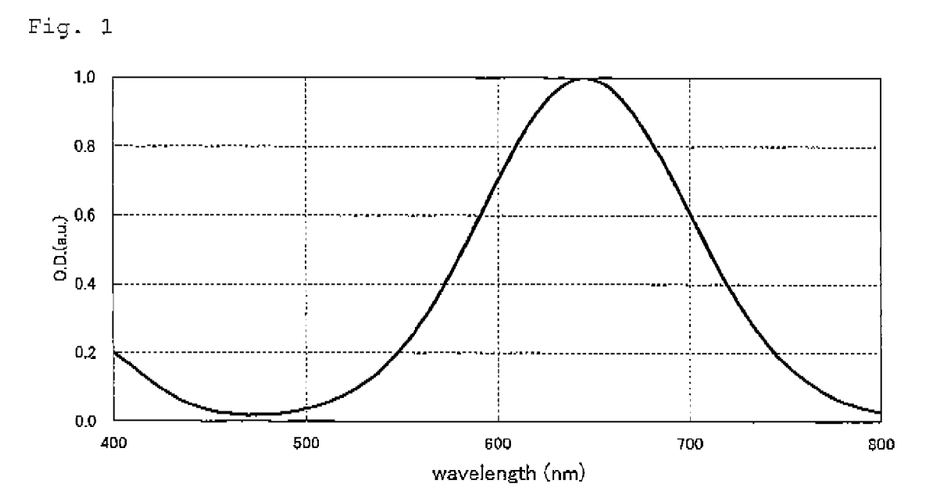
FIG. 1 is a reflection spectrum of the image obtained in the inkjet recording in the example.

The thus-obtained ink was filled in a cartridge of an inkjet printer (PM-G800, trade name by Seiko Epson), and tested in the printer for image recording on inkjet paper, Kassai Photo-finish Pro (trade name by FUJIFILM). The reflection spectrum of the thus-formed image is shown in FIG. 1. As is obvious from the data in FIG. 1, it is known that the obtained image has excellent spectral characteristics and the ink has excellent properties as inkjet ink.

Example 5

Construction and Evaluation of Color Filter

<Construction of Color Filter>

(Preparation of Positive Resist Composition)

3.4 parts by mass of cresol/novolak resin obtained from a mixture of m-cresol/p-cresol/formaldehyde (reaction molar ratio=5/5/7.5) (polystyrene-based mass-average molecular weight, 4300), 1.8 parts by mass of o-naphthoquinonediazido-5-sulfonate ester produced by the use of a phenol compound having a formula mentioned below (in which 2 hydroxyl groups were esterified on average), 0.8 parts by mass of hexamethoxymethylolated melamine, 20 parts by mass of ethyl lactate, and 1 part by mass of the compound (1) were mixed to produce a positive resist composition.

Phenolic Compound:

(Construction of Color Filter)

The obtained positive resist composition was applied onto a silicon wafer in a mode of spin coating, and the solvent was evaporated away. Next, the silicon wafer was exposed to light through a mask to decompose the quinonediazide compound. Next, this was heated at 100° C. and then the exposed area was removed by alkali development to obtain a positive color pattern having a resolution of 0.8 μm. This was exposed on the entire surface, and then heated at 150° C. for 15 minutes to produce a cyan-complementary color filter. For the exposure, used was an i-ray exposure stepper HITACHI LD-5010-i (trade name by Hitachi, NA=0.40). As the developer, used was SOPD or SOPD-B (trade name by Sumitomo Chemical Industry).

<Evaluation>

Figure 2:
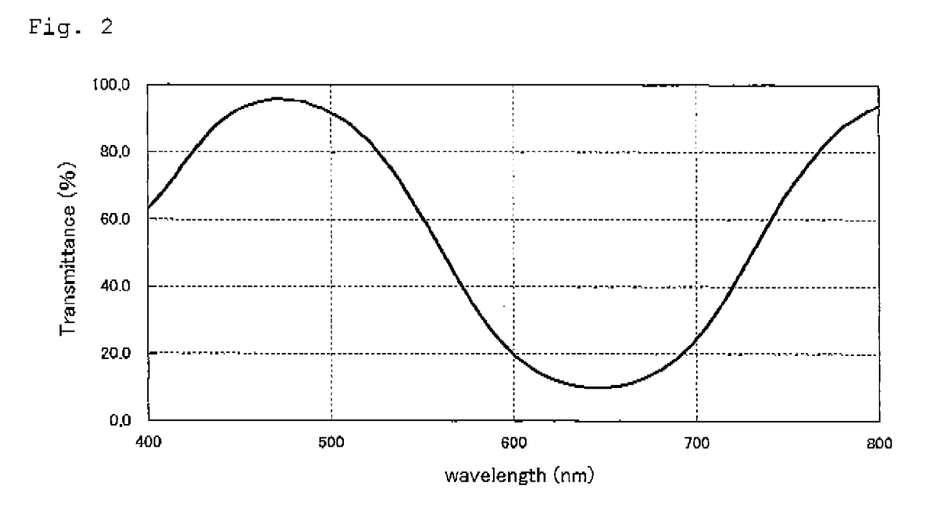
FIG. 2 is a transmission spectrum of the color filter produced in the example.

The transmission spectrum of the obtained color filter is shown in FIG. 2. As is obvious from the data in FIG. 2, the obtained color filter has excellent spectral characteristics and light transmittance, and has excellent properties as color filter.

According to the invention, there are provided a novel indaniline dye having excellent spectral characteristics with sharp absorption, high fastness and excellent solubility, and a coloring composition containing the indaniline dye. According to the invention, there are also provided a thermal transfer recording ink sheet and a thermal transfer recording method capable of satisfying all the requirements of excellent color reproducibility, image storability and transfer sensitivity in print samples. The ink sheet is excellent in that the working load and the environmental load in producing it are greatly reduced, Further, the invention provides a color toner, an inkjet ink and a color filter comprising the indaniline dye.

Accordingly, the invention is expected to be effectively used in high-quality full color recording, and its industrial applicability is great.

The present disclosure relates to the subject matter contained in Japanese Patent Application No. 092235/2007 filed on Mar. 30, 2007, which is expressly incorporated herein by reference in its entirety. All the publications referred to in the present specification are also expressly incorporated herein by reference in their entirety.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined claims set forth below.

What is claimed is:

1. An indaniline dye represented by the following formula (1):

wherein $R^1$ and $R^2$ each independently represent an unsubstituted linear or branched alkyl group having from 2 to 5 carbon atoms; $R^3$ represents an unsubstituted linear or branched alkyl group having from 1 to 3 carbon atoms; provided that the total number of the carbon atoms of $R^1$, $R^2$ and $R^3$ is 6 or 7.

2. A thermal transfer recording ink sheet containing the indaniline dye of claim 1.

3. A thermal transfer recording method comprising forming an image by use of the thermal transfer recording ink sheet of claim 2 on an image-receiving material comprising a polymer-containing ink-receiving layer on a support.

4. A color toner containing the indaniline dye of claim 1.

5. An inkjet ink containing the indaniline dye of claim 1.

6. A color filter containing the indaniline dye of claim 1.

* * * * *